United States Patent [19]

Nickell et al.

[11] Patent Number: 4,826,526

[45] Date of Patent: May 2, 1989

[54] 1,3,5-TRIAZINE-2-ONE DERIVATIVES AND THEIR USE AS PLANT GROWTH REGULATORS

[75] Inventors: Louis G. Nickell, Chicago; Leonard J. Stach, Riverside; Frank Wu, Libertyville, all of Ill.

[73] Assignee: Sandoz Ltd., Basel, Switzerland

[21] Appl. No.: 242,860

[22] Filed: Sep. 9, 1988

Related U.S. Application Data

[63] Continuation of Ser. No. 59,994, Jun. 9, 1987, abandoned, which is a continuation of Ser. No. 931,753, Nov. 17, 1986, abandoned, which is a continuation of Ser. No. 801,890, Nov. 26, 1985, abandoned.

[51] Int. Cl.$^4$ .................. A01N 43/66; C07D 251/04

[52] U.S. Cl. .......................................... 71/74; 71/93; 544/215

[58] Field of Search ...................... 544/215; 71/93, 74

[56] References Cited

PUBLICATIONS

Chem. Abstracts vol. 107, No. 19; 176070q (1987).

*Primary Examiner*—Robert W. Ramsuer
*Assistant Examiner*—J. Richter
*Attorney, Agent, or Firm*—Gerald D. Sharkin; Richard E. Vila

[57] ABSTRACT

This application discloses the compound 3-(2-chloropyridin-4-yl)-5-methyl-1-phenyl-1,3,5-triazin-2-one. This compound is useful in increasing the size of grapes, as a cotton defoliant, and as a herbicide.

8 Claims, No Drawings

1,3,5-TRIAZINE-2-ONE DERIVATIVES AND THEIR USE AS PLANT GROWTH REGULATORS

This is a continuation of application Ser. No. 59,994, filed June 9, 1987, now abandoned, which in turn is a continuation of application Ser. No. 931,753, filed Nov. 17, 1986, now abandoned, which in turn is a continuation of application Ser. No. 801,890, filed Nov. 26, 1985, now abandoned.

This invention relates to the new compound, 3-(2-chloropyridin-4-yl)-5-methyl-1-phenyl-1,3,5-triazin-2-one and to its use to increase the size of grapes and to defoliate cotton.

This compound can be prepared as follows:

EXAMPLE 1

Preparation of 3-(2-Chloropyridin-4-yl)-5-Methyl-1-Phenyl 1,3,5-Triazin-2-One Formaldehyde (15 mol, 98% aqueous solution) was added dropwise to a mixture of N-(2-chloro-4-pyridinyl)-N'-phenylurea (3.0 grams; 0.012 mole), methylamine (15 ml, 40% aqueous solution) and methanol (20 ml) in a three-necked reaction flask equipped with stirrer, thermometer and addition funnel. This reaction mixture was stirred for twenty hours at room temperature and then evaporated by Gredwood presure to give the desired product as a pale yellow oil (4.0 grams). This product analyzed as follows:

|  | Theoretical (%) | Found (%) |
| --- | --- | --- |
| Carbon | 59.50 | 57.15 |
| Hydrogen | 4.99 | 5.56 |
| Nitrogen | 18.51 | 19.60 |

Unexpectedly it has been found that the size of grapes can be increased by applying to the grapes an effective amount of the compound 3-(2-chloropyridin-4-yl)-5-methyl-1-phenyl-1,3,5-triazin-2-one.

The term grapes as used herein means Vitis generally and includes, for example, Thompson Seedless, Perlette, Rebeir, Seedless Tokay and Interlocken.

In practicing the invention it is important to realize that the effectiveness of the compound on grape varies from season to season and from vine to vine. Therefore, application of the compound will result in different increases in the size of the berries depending upon the time of application. Generally, the compounds should be applied at from about 10 days post-bloom to about two weeks prior to the intended harvest time.

The compounds are applied at a rate of from 5 to 300 grams per acre and 50 to 100 grams is optimal. Above 400 grams per acre the phytotoxicity is excessive.

The compound is employed in the form of an aqueous solution or dispersion. Generally where the application device is spray gun, boom or other device where the solution is expressed through a narrow orifice by pressure, the application rate is 50 to 200 gallons of solution per acre. Where the application is by means of an air sprayer (e.g. a "speed sprayer"), i.e. the solution is entrained in a fast moving air stream, more concentrated solutions are employed and about 5 to 50 gallons per acre can be used. Regardless of the amount of solution employed, the grams of active ingredients per acre should be within the ranges described above.

In the aqueous solutions employed, it is preferred to use a surfactant to prevent the solution from forming globules and "rolling off" upon contact with the leaves of the plant. The surfactant level is generally from 0.1 to 15% by volume of the total formulation and 0.1 to 1.5 preferred. Suitable surfactants which can be employed include: sorbitan monolaurate, sorbitan monopalmitate, sorbitan monostearate, sorbitan monooleate, sorbitan trioleate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, polyoxyethylene cetyl ether, polyoxyethylene stearyl ether and polyoxyethylene oleyl ether.

The above materials are commonly available under trade names such as "Tween", "Span", "Brij", and "Carbowax". Other surfactants which reduce tension can also be employed.

In order to determine the usefulness of 3-(2-chloropyridin-4-yl)-5-methyl-1-phenyl-1,3,5-triazin-2in increasing the size of grapes, tests were performed on two varieties of grapes: Thompson Seedless and Perlette. In the tests the compound was applied at 10, 50, and 100 ppm. A stock solution was developed by diluting 0.2 grams of the compound into 20 ml of acetone. The stock solution was diluted to a volume of 500 ml by diluting 5 ml. of the stock solution with 495 ml of water. This solution was then further diluted with water to the test concentration and a drop of Triton B1956 was added to each dip solution cup and stirred prior to dipping grape bunches into the solution.

Ten bunches on one grape vine were dipped into each solution. Adjacent vines were used for each treatment. The remaining fruit on the vines was left intact. Treatments were made when most of the bunches were in the two week post-bloom period. Post-treatment evaluations were made 34 days after treatment. The size of the grape was determined on a scale of 1-5, where 1=no increase and 5=a maximum increase. Similarly the phytotoxicity to the grape was determined on a scale of 1-5, where 0=no phytotoxicity and 5 =dead berries, as follows:

|  |  | Rate of Application (ppm) | | | |
| --- | --- | --- | --- | --- | --- |
| Grape | Property | 0 | 10 | 50 | 100 |
| Thompson Seedless | Size increase | 1 | 2 | 3 | 4 |
|  | Phytotoxicity | 0 | 1 | 3 | 3 |
|  | Weight (grams) | 1.5 | 2.1 | 2.9 | 2.2 |
| Perlette | Size increase | 1 | 2.5 | 3 | 3 |
|  | Phytotoxicity | 0 | 0.5 | 1 | 2 |
|  | Weight (grams) | 2.1 | 3.0 | 3.2 | 2.8 |

In addition it has been found that 3-(2-chloropyridin-4-yl)-5-methyl-1-phenyl-1,3,5-triazin-2-one is an effective cotton defoliant.

In order to determine the usefulness of 3-(2-chloropyridin-4-yl)-5-methyl-1-phenyl-1,3,5-triazin-2cotton plants were grown in the greenhouse under high intensity illumination. At the seven true-leaf stage, the cotton plants were foliarly treated to run off with the test compound, three plants per treatment.

Data were recorded three weeks after application of the test compound. The value for each system is a score relative to a scale of 0-10. The data represent averages for 3 plants per treatment. The value for necrosis (N) indicates a relative proportion of leaf tissue which has died. Leaf abscission (D) is based on the leaves present at the time of application of the test compound, while regrowth is described by apical meristem damage (M) and growth from axillary buds (A).

| Rate of Application | N | M | D | A |
|---|---|---|---|---|
| 200 | 3.3 | 8.0 | 9.3 | 4.3 |
| 100 | 4.0 | 5.0 | 8.0 | 2.7 |
| 50 | 1.7 | 0.0 | 7.3 | 0.3 |

As a defoliant for cotton, the compound is applied as an aqueous solution preferably containing from about 50 to about 500 ppm of the compound. It is applied to the cotton plants in an effective amount. In order to ensure that an effective amount is applied to the cotton plant, it is applied to run off the plants. It can be applied to the cotton plant from about 10 to about 30 days prior to harvest.

In addition to its utility as a cotton defoliant and to increase the size of grapes, it is also an effective herbicide.

The herbicidal utility of the new compound of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the test compound formulated as an aqueous emulsion of acetone solution containing emulsifiers was sprayed at eight pounds per acre on the surface of the soil.

After spraying, the soil containers were placed in the greenhouse and provided with supplementary heat as required and daily or more frequent watering. The plants were maintained under these conditions for a period of 21 days, at which time the condition of the plants and the degree of injury to the plants was rated on a scale of from 0 to 10, as follows: 0=injury; 1, 2=slight injury; 3, 4=moderate injury, 5, 6=moderately severe injury; 7-9=severe injury; and 10=death. The effectiveness of this compound is demonstrated by the following data.

| Plant | Rating |
|---|---|
| Velvetleaf | 8 |
| Pigweed | 2 |
| Crabgrass | 8 |

-continued

| Plant | Rating |
|---|---|
| Barnyard grass | 4 |
| Yellow foxtail | 4 |

The herbicidal activity of the compound of this invention was also demonstrated by experiments carried out for the post-emergence control of a variety of weeds. In these experiments the compound was formulated as an aqueous emulsion and sprayed at the indicated dosage on the foliage of the weeds that have attained a prescribed size. After spraying, the plants were placed in a greenhouse and watered daily or more frequently. Water was not applied to the foliage of the treated plants. The severity of the injury was determined 14 days after treatment and was rated on the scale of from 0 to 10 heretofore described. The effectiveness of the compound is demonstrated by the following data:

| Plant | Rating |
|---|---|
| Velvetleaf | 8 |
| Pigweed | 10 |
| Crabgrass | 7 |
| Barnyard grass | 7 |
| Yellow foxtail | 8 |

We claim:
1. 3-(2-chloropyridin-4-yl)-5-methyl-1-phenyl-1,3,5-triazin-2-one.
2. A method for increasing the size of grapes which comprises applying to the grape plants an effective amount of the compound of claim 1.
3. The method of claim 2 wherein the compound of claim 1 is applied to the grapes from about 10 days post-bloom to about 2 weeks prior to harvest.
4. The method of claims 2 or 3 wherein the amount of the compound of claim 1 applied to the grape plants is from 5 to 300 grams per acre.
5. A method for defoliating cotton which comprises applying to the cotton plants an effective amount of the compound of claim 1.
6. The method of claim 5 wherein the compound of claim 1 is applied to run off.
7. The method of claim 6 wherein the compound of claim 1 is applied from a solution containing from about 50 to about 500 ppm of said compound.
8. The method of claims 5 or 6 wherein the compound of claim 1 is applied from about 10 to about 30 days prior to harvest.

* * * * *